United States Patent [19]

Barnwell

[11] Patent Number: 4,543,094

[45] Date of Patent: Sep. 24, 1985

[54] SYRINGE AND ACCESSORY

[76] Inventor: John K. Barnwell, 6365 Susan Dr., Mableton, Ga. 30059

[21] Appl. No.: 591,003

[22] Filed: Mar. 19, 1984

[51] Int. Cl.$^4$ .............................................. A61M 5/00
[52] U.S. Cl. ....................................... 604/236; 604/89
[58] Field of Search ................. 604/236, 30, 32, 187, 604/232, 191, 207, 248, 89

[56] References Cited

U.S. PATENT DOCUMENTS 3,757,981  9/1973  Harris, Sr. et al. ................. 604/414
3,952,729  4/1976  Libman et al. ................... 604/236 X
4,044,758  8/1977  Patel ..................................... 604/191
4,381,778  5/1983  Kozam et al. ....................... 604/191

Primary Examiner—John D. Yasko
Attorney, Agent, or Firm—Thomas & Kennedy

[57] ABSTRACT

A syringe has a chamber isolated from an open ended barrel. A valve provides fluid communication between the chamber and barrel and an outlet. In an alternative form the chamber is within a structurally independent cell that may be mounted to a conventional syringe in piggyback fashion.

10 Claims, 3 Drawing Figures

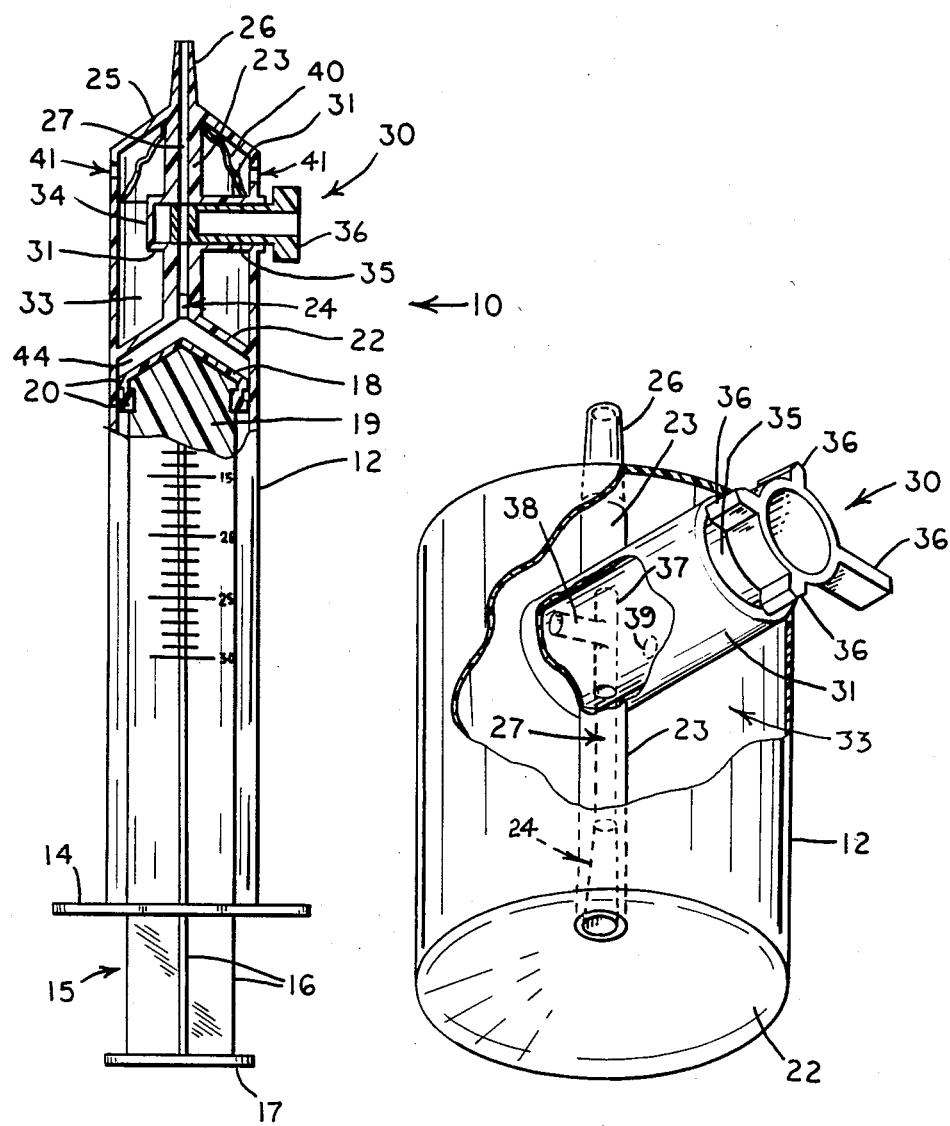

SYRINGE AND ACCESSORY

TECHNICAL FIELD

This invention relates to syringes such as those used to store and administer medications.

BACKGROUND OF THE INVENTION

Drugs and medications administered by injection, as with a hypodermic needle and syringe, are often comprised of constituents that if mixed together and stored for a long period of time tend to degrade in one manner or another. Degradation can also occur to medications when they are stored in their fully diluted state for long periods. For these reasons medication constituents are typically mixed just prior to injection as by, for example, drawing them into a syringe from sealed vials. Sometimes, however, a phenomenon known as "blowback" occurs when a hypodermic needle is injected into or removed from such a vial whereupon some of the medication squirts free to ambiance. Blowback creates a dangerous situation since many drugs, though safe and effective when used internally as prescribed, are hazardous to external skin and to facial features such as the eyes. Indeed, many such drugs are carcinogenic or antineoplastic. Even some antibiotics and antimicrobials can be harmful. Blowback is also a hazard in the administration of a single drug since such is normally stored in a sealed vial, rather than within a syringe, which seal must be pierced in withdrawing the drug from the vial into the syringe.

To overcome these problems and others, mixing syringes have recently been developed as exemplified by those disclosed in U.S. Pat. Nos. 3,351,058, 3,380,451, 3,684,136, 3,881,485, 4,059,109, 4,159,109, 4,226,236 and 4,306,554. Though some of these syringes have tended to alleviate the problem of blowback, they have not been problem-free. For example, they are often designed so that they are easily activated by external pressure such as by finger pressure applied to a flexible housing as in a pinching motion or by accidental movement of their externally accessible plunger. Other mixing syringes, which are provided with frangible diaphragms that are pierced by the action of an internal needle in order to provide fluid communication between independent chambers, may also be easily actuated prematurely. Still others, which are provided with pressure operable flaps, are also susceptible to being prematurely operated and to having their contents be poorly mixed. In addition, in cases where medication constituents are housed within a frangible bulb within a syringe barrel, which bulb is crushed to establish fluid communication for mixing, there is the risk that some of the bulbous fragments may be ejected from the mixing syringe. This is also the case with the previously mentioned syringes that have frangible diaphragms. Many of these prior art syringes must also be made of plastic for flexibility, which is disadvantageous in cases where a drug to be administered therewith has a plasticizer that can leach into the plastic syringe material.

It thus is seen that syringe and vial systems and mixing syringes of the prior art have had distinct problems and limitations. Accordingly, the present invention seeks to provide apparatus which tends to alleviate these problems.

SUMMARY OF THE INVENTION

In one form of the invention a syringe comprises a tubular housing having a needle end formed with an outlet and an open plunger end. A partition is provided within the housing separating a rear chamber located proximal the plunger end and a forward chamber located distal the plunger end. The syringe also has conduit means for providing communication between the outlet, the forward chamber and the rear chamber. Valve means are provided for alternatively establishing exclusive communication through the conduit means between the forward and rear chambers and between the outlet and rear chamber. Finally, a plunger is movably mounted within the rear chamber.

In another form of the invention, a syringe comprises a tubular housing having a barrel open at one end in which a plunger is slidably positioned, and a storage chamber separated from the barrel by a partition. A conduit extends through the partition and the storage chamber to a needle mount orifice and which conduit has an outlet opening into the chamber. Three-way valve means are associated with the conduit for selectively providing fluid communication through the conduit between the needle mount orifice and the storage chamber for loading the storage chamber with a medication, for fluid communication between the storage chamber and the barrel for drawing medication from the chamber into the barrel upon actuation of the plunger, and for providing fluid communication between the barrel and the needle mount orifice for medication ejection.

In yet another form of the invention apparatus for separately storing, mixing and ejecting a medication comprises a syringe having a tubular coupling at one end and plunger means operatively extending out of the other end. The apparatus also has a cell adapted to house a medication that has a chamber, a tubular coupling adapted to be coupled with the syringe coupling, another tubular couling adapted to be coupled with a needle, a conduit mounted within the chamber extending between the cell couplings which has an opening into the chamber, and valve means for selectively controlling the flow of medication between the cell couplings and the opening.

In still another form of the invention apparatus for storing and supplying medication to a syringe when mounted thereto comprises a cell having a conduit extending therethrough between two externally accessible tubular couplings and having an orifice opening into the cell interior. Valve means are also provided for controlling the flow of medication through the conduit. So constructed, the cell may be filled with medication with the valve means establishing communication between one of the couplings and the orifice through the conduit, the cell contents drawn into the syringe with the valve means establishing communication between the orifice and the coupling to which the syringe is coupled, and medication expelled to ambiance through the cell conduit with the valve means establishing communication between the two cell couplings.

BRIEF DESCRIPTION OF THE DRAWING

FIG. 1 is a side elevational view, shown partly in cross-section, of a syringe embodying principles of the present invention.

FIG. 2 is a perspective view of a portion of the syringe shown in FIG. 1 with a portion thereof shown broken away to reveal internal features.

DETAILED DESCRIPTION

Figure 3:
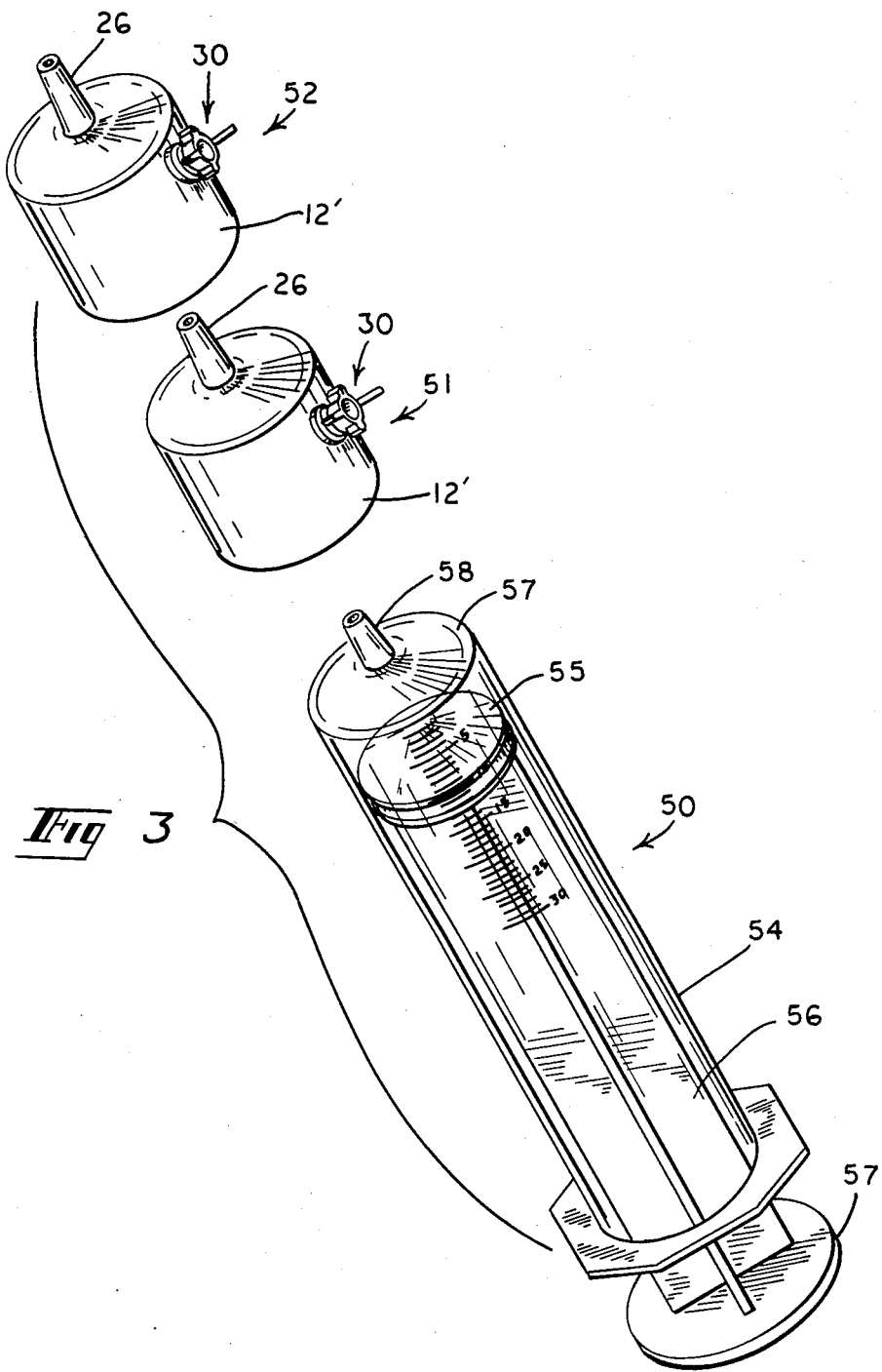
FIG. 3 is a perspective view of apparatus embodying principles of the invention in an alternative form.

With reference next to the drawing, there is shown in FIG. 1 a syringe 10 having a transparent, cylindrical barrel 12 having an annular flange 14 formed at a proximal, open end out of which projects a plunger rod 15 formed of cross-ribs 16. A push plate 17 is formed on the exposed end of the plunger rod 15 while a rubber plunger 18 is mounted upon a plunger support 19 formed at the other end of the plunger rod. The resilient, rubber plunger 18 is formed with two annular ribs 20 positioned in intimate, rubbing, sealing relationship with the cylindrical inner surface of the barrel 12. Thus, the plunger assembly is of conventional construction.

With continued reference to FIG. 1, the syringe is further seen to have a conically shaped wall or partition 22 located adjacent to the plunger 18 with its surface conformed to that of the plunger. A tube or conduit having a tapered female coupling end 24 extends from the partition 22 along the axis of the syringe barrel to a conically shaped distal syringe end wall 25. Here, the central tube 23 merges with an exposed male coupler 26. Together the coupler 26 and central tube 23 form a central conduit or passageway 27 to provide fluid comunication between ambiance and an interior chamber 44 of the syringe.

The syringe is also seen to include a three-way valve shown generally at 30, the details of which may be best seen by reference to FIG. 2 which shows in enlarged detail that portion of the syringe illustrated in FIG. 1 which extends from the partition 22 to the male coupling 26. Valve 30 includes a transverse, tubular housing 31 which extends across the axis of the syringe cylinder partially through a chamber 33 located between the partition 22 and the end wall 25. It thus merges with the central conduit 23. The housing extends to the exterior of the barrel where it is open ended while its other end 34 is closed. Within the housing 31 is rotatably mounted a valve tube 35, a portion of which extends out of the open end of the housing 31 to a handle 36. The handle has three angularly spaced position indicators 36. The valve tube 31 is formed with a T-shaped conduit having a main conduit 37 and a branch conduit 38. The T-shaped conduit is positioned for rotary movement about a point located along the cylindrical axis for alignment with an aperture 39 formed in the valve housing 31 to provide, in selective rotary positions, fluid communication between the T-shaped conduit and chamber 33 via aperture 39. Finally, a flexible diaphragm 40, which is not shown in FIG. 2 for clarity, is mounted within the chamber 33 over a set of ports 41 provided at angularly spaced intervals about the periphery of the barrel adjacent the barrel end 25.

In use, the chamber 33 may be loaded with a medication by positioning the valve 30 so as to provide fluid communication between the coupler 26 and the chamber 33. Once chamber 33 is loaded the valve is rotated so as to seal off the chamber from ambiance as positionally illustrated in FIG. 2. In this position it should be noted that fluid communication is established between couplers 24 and 26 through conduit 27. Alternatively, the valve may be rotated 45° from its illustrated position thereby blocking communication between the chamber 33 and conduit 27 as well as communication between couplers 24 and 26. When it becomes time to administer the medication, the valve is rotated to establish exclusive communication between aperture 39 and coupler 24, and plunger rod 15 is pulled outwardly from barrel 12. The stored medication is thereby drawn from chamber 33 into the expanding chamber 44. Complete withdrawal may be facilitated by the provision of a tube (unshown) extending from aperture 39 to the bottom of the chamber. During this time backpressure is prevented from occuring by movement of the diaphragm 40 and the entry of ambient air through ports 41 behind the diaphragm. Once the properly measured quantity of medication has been drawn into chamber 44, as observed from the barrel calibrations, the valve is again rotated to the position illustrated in FIG. 2 thereby establishing fluid communication between the chamber 44 and the coupler 26 for ejection from the syringe as into a patient via a needle mounted to the coupler.

With reference next to FIG. 3 another embodiment of the invention is seen to include a conventional syringe 50 to which two cells or vials 51 and 52 may be successively mounted in successive "piggy-back" fashion. Each of the cells is of the same construction as the structure illustrated in FIG. 2. Here, however, the cells are structurally disjoined from the syringe whereas the "cell" of FIG. 2 is a unitary portion of the syringe 10. Thus, in FIG. 3 neither cell 51 nor 52 contains that portion of the syringe 10 that extends from partition 22 to flange 14 as shown in FIG. 1, nor the plunger movably positioned therein.

The syringe 50 is conventional and is seen to be comprised of a cylindrical barrel 54 having a rubber plunger 55 positioned in sliding, sealing engagement with the interior wall of the barrel. A plunger rod 56 extends from the plunger 55 to ambiance out of the open end of the barrel to a plate 57. The other end of the barrel 54 has conical end wall 57 from which a male coupler 58 projects along the axis of the syringe barrel.

Each of the two cells 51 and 52 has a cylindrical wall or barrel 12' which, again, differs from that of the embodiment shown in FIG. 1 and 2 only in that it terminates with partition 22. Each cell also has the three-way rotatable valve couplers 24 and 26. The cells 51 and 52 are loaded with a medication by positioning the valve 30 so as to provide fluid communication between the cell interior chamber and ambiance through either coupler 24 or 26. The valve is then positioned so as to seal off the interior from ambiance for storage. For ejection, the cells are mounted in piggy-back fashion to the syringe 50 with syringe coupler 58 mated with coupler 24 of cell 51 and with coupler 26 of cell 51 mated with coupler 24 of cell 52. By operation of the valves 30 of the cells 51 and 52, and the withdrawal of syringe plunger 55 by manual movement of the plate 57, the contents of the two cells 51 and 52 may be drawn into the barrel 54 of the syringe 50 and mixed. Thus, the contents of one of the cells may be in the form of a granulated medication constituent such as a solute. Alternatively, the medications housed in mutual isolation in the two cells may be both in a liquid state. The cells may either be left in a mounted configuration upon the syringe or removed for ejection. When the two cells are left upon the syringe, their valves 50 are rotated so as to provide for the free flow of fluid through their conduits 27 unimpeded by the valves. By actuation of the syringe plunger the mixed medication may now be ejected from the syringe 50 through the channels 27 of the two cells 51 and 52 to ambiance or the cells dismounted and the mixed medication ejected to ambiance from the syringe coupler 26.

The versatility of the embodiment shown in FIG. 3 is quite pronounced. For example, instead of two cells it will be noted that one, three or even more cells may be independently selected and mounted in piggy-back fashion to a syringe for mixing their constituents together after having been stored and without fear of blowback. Mixing ratios may be easily measured by reference to the calibrations marked on the barrel exterior during medication withdrawal from each cell.

It thus is seen that a syringe and syringe accessory in the form of one or more cells is provided which overcomes problems and limitations of the prior art. It should, however, be understood that the just described embodiments merely illustrate principles of the invention in two preferred forms. Many modifications, additions and deletions other than those expressly suggested may, of course, be made thereto without departure from the spirit and scope of the invention as set forth in the following claims.

I claim:

1. A syringe comprising a tubular housing having a barrel open at one end in which a plunger is slidably positioned and a storage chamber separated from said barrel by a partition; a conduit extending through said partition and said storage chamber to a needle mount orifice and having an outlet opening into said chamber; and three-way valve means associated with said conduit for alternatively providing fluid communication through said conduit between said needle mount orifice and said storage chamber for loading said storage chamber with a medication, for fluid communication between said storage chamber and said barrel for drawing medication from said chamber into said barrel upon actuation of said plunger, and for providing fluid communication between said barrel and said needle mount orifice for medication ejection.

2. The syringe of claim 1 wherein each alternative fluid provided by said three-way valve means is exclusive.

3. The syringe of claim 1 wherein said three-way valve means comprises a T-shaped conduit.

4. Apparatus for separately storing, mixing and ejecting a medication comprising:

a syringe having a tubular coupling at one end and plunger means operatively extending out of the other end; and a cell having a chamber adapted to house a medication, a tubular coupling adapted to be coupled with said syringe coupling, another tubular coupling adapted to be coupled with a needle, a conduit mounted within said chamber extending between said cell couplings and having an opening into said chamber, and valve means for selectively controlling the flow of medication between said cell couplings and said opening.

5. The apparatus of claim 4 further comprising a second cell having a chamber adapted to house another medication and having the same structure as said cell whereby the second cell may be mounted in tandem to said cell.

6. The apparatus of claim 4 wherein said valve comprises a rotatable T-shaped conduit.

7. Apparatus for storing and supplying medication to a syringe when mounted thereto and with said apparatus comprising a cell having a conduit extending therethrough between two externally accessible tubular couplings and having an orifice opening into the cell interior, and valve means for controlling the flow of medication through said conduit, whereby the cell may be filled with medication with the valve means establishing communication between one of the couplings and the orifice through the conduit, the cell contents drawn into the syringe with the valve means etablishing communication between the orifice and the coupling to which the syringe is coupled, and medication expelled to ambiance through the cell conduit with the valve means establishing communication between the two cell couplings.

8. The apparatus of claim 7 wherein said valve means comprises a rotatably three-way valve.

9. The apparatus of claim 8 wherein said valve means comprises a rotatable T-shaped conduit.

10. The apparatus of claim 9 wherein said T-shaped conduit is mounted to a cylindrical arm that extends through a tubular member mounted within said cell to the exterior of said cell for manual accessibility, and wherein said tubular member has three holes angularly spaced for a plurality of alignments with conduit members of said rotatable T-shaped conduit.

* * * * *